United States Patent [19]

Broughton et al.

[11] Patent Number: 5,539,089
[45] Date of Patent: Jul. 23, 1996

[54] A83543 AGLYCONES AND PSEUDOGLYCONES

[75] Inventors: Mary C. Broughton; Lawrence Creemer, both of Indianapolis; Mary L. B. Huber, Danville; Herbert A. Kirst, Indianapolis; Jan R. Turner, Carmel, all of Ind.

[73] Assignee: DowElanco, Indianapolis, Ind.

[21] Appl. No.: 301,835

[22] Filed: Sep. 7, 1994

Related U.S. Application Data

[63] Continuation of Ser. No. 137,697, Oct. 15, 1993, abandoned, which is a continuation of Ser. No. 790,616, Nov. 8, 1991, abandoned.

[51] Int. Cl.$^6$ .......................... C07H 17/08; C07D 305/00
[52] U.S. Cl. .......................... 536/6.5; 536/18.1; 549/264
[58] Field of Search .......................... 536/7.1, 18.1; 549/264; 514/28

[56] References Cited

U.S. PATENT DOCUMENTS

| | | | |
|---|---|---|---|
| 4,148,883 | 4/1979 | Celmer et al. | 424/122 |
| 4,206,206 | 6/1980 | Mori et al. | 424/167 |
| 4,224,314 | 9/1980 | Celmer et al. | 424/122 |
| 4,251,511 | 2/1981 | Whaley et al. | 424/122 |
| 4,293,651 | 10/1981 | Whaley et al. | 535/169 |
| 4,321,329 | 3/1982 | Whaley et al. | 535/253 |
| 4,448,970 | 5/1984 | Magerlein | 548/336 |
| 4,501,752 | 2/1985 | Yokoi et al. | 514/414 |
| 4,515,942 | 5/1985 | Iwasaki et al. | 536/16.8 |
| 4,831,016 | 5/1989 | Mrozik et al. | 536/7.1 |

FOREIGN PATENT DOCUMENTS 375316  12/1989  European Pat. Off.

OTHER PUBLICATIONS

Borck et al., Chemical Abstracts, vol. 114 (1991) No. 80066m.
Kirst et al., Tetrahedron Leters (1991), 32(37):4839–4842.
Whaley et al., Tetrahedron Ltr. (1980), 21:3659.
Kreuzman et al., J. Biological Chemistry (1988), 263(30):15626–15633.
Snyder et al., J. Am. Chem Soc., (1984) 106:787.
Mertz and Yao, Int'l J of Systematic Bacteriology (1990), 40(1);34–39.
Celmer et al., J. Chem. Soc. (1980) 102:4203.
Aizawa et al. (1979), The Journal of Antibiotics, 22(3):193–196.
Ikeda, et al. (1985), J. Antibiotic, 38:436.
Jomon et al., (1972), The Journal of Antibiotics, 25(5):271–280.
Dybas and Babu (1988), Brighton Crop Protection Conference, 57–64.
Borchardt et al. (1979), Biochem. & Biophys. Res. Comm., 89(3):919–924.
Vedel et al., (1978), Biochem. & Biophys. Res. Comm., 85(1):371–376.
Pickett, J. A., (1988), Chemistry in Britain, 137–142.
Omura, (1984), Macrolide Antibiotics, Chapter 13.
Fuller (1978), Biochemical Pharmacology, 27:1981–1983.
Jackson et al. (1988), Abstracts of the 1988 ICAAC, 26026.
Umezawa (1980), The Journal of Antibiotics, 33(3):15–26.
Umezawa, Index of Antibiotics from Actinomycetes, vol. 2.
Omura and Tannaka (1984), Macrolide Antibiotics Chapter 1.
Schulman and Ruby (1987), Antimicrobial Agents and Chemotherapy, 31(6):964–965.
Schulman et al (1985), The Journal of Antibiotics, 1494–1498.
Ito and Hirata (1972), Tetrahedron Letters, 12:1185–1188.
Aizawa et al. (1979), J. Antibiot. 32:193.
Ito et al. (1972), Tetrahedron Letters, 11–81, 1185, 2557.
Aizawa et al., (1979), J. Antibiot., 32:193.
Derwent Abstract 84–278337/45, SSSE Mar. 16, 1983.
Derwent Abstract 84–252941/41, SSSE Feb. 16, 1983.
Derwent Abstract 92:144960k.
Derwent Abstract 11667c/07, KAKE May 31, 1978.
Derwent Abstract 92:211459u.
Derwent Abstract 88–095030/14, SSSE 00.00.86.
Derwent Abstract 85–245719/40, SSSE Feb. 1, 1984.
Derwent Abstract 54333S–BCD, Fuji, Feb. 17, 1969.
Derwent Abstract 80–11667C/07.
Catalogue of bacteria and phages, ATCC, 7th Ed., 1989.
Umezawa, Institute of Microbial Chemistry, Tokyo, Index of Antibi, from Actinomycetes, vol. I.
Umezawa, Supplement of Index of Antibiotics from Actinomycetes.

*Primary Examiner*—Elli Peselev
*Attorney, Agent, or Firm*—Andrea T. Borucki

[57] ABSTRACT

A83543 Aglycones A83543AgA, A83543AgD, A83543AgE, and A83543AgF, and A83543 pseudoaglycones A83543PsaA2, A83543PsaB2, A83543PsaD2, and A83543PsaN2 are intermediates useful in preparation of known insecticides.

8 Claims, No Drawings

A83543 AGLYCONES AND PSEUDOGLYCONES

CROSS-REFERENCE TO RELATED APPLICATION

This is a continuation of application Ser. No. 08/137,697 filed Oct. 15, 1993, now abandoned, which is a continuation of 07/790,616, filed on Nov. 8, 1991, which is now abandoned.

BACKGROUND OF THE INVENTION

This invention provides new macrolide compounds that are useful intermediates for production of known macrolide insecticides.

Fermentation product A83543, a family of related factors produced by *Saccharopolyspora spinosa*, was recently discovered and was shown to exhibit excellent insecticidal activity. European Patent Application No. 0 375 316 A1 discloses factors A83543A, A83543B, A83543C, A83543D, A83543E, A83543F, A83543G, A83543H, and A83543J, as well as the six pseudoaglycones, A83543PsaA1, A83543PsaD1, A83543PsaE1, A83543PsaF1, A83543PsaH1, and A83543PsaJ1, which are produced by removing the amino sugar from A83543A, A83543D, A83543E, A83543F, A83543H, and A83543J, respectively. Removing the amino sugar from factor A83543B, A83543C, or A83543G also produces A83543PsaA1.

The U.S. patent application of Jon S. Mynderse, James W. Martin, and Jan R. Turner on "New A83543 Compounds and Processes for Production Thereof" (U.S. application Ser. No. 07/790,287) filed on Nov. 8, 1991, and now abandoned is hereby incorporated herein by reference. That application discloses factors A83543L, A83543M, and A83543N, as well as the pseudoaglycone A83543PsaL1, which is produced by removing the amino sugar from A83543L or A83543N. Removing the amino sugar from A83543M produces A83543PsaJ1.

The following table identifies by structure these known A83543 compounds.

| Factor | $R^{1'}$ | $R^{2'}$ | $R^{3'}$ | $R^{4'}$ | $R^{5'}$ | $R^{6'}$ |
|---|---|---|---|---|---|---|
| A83543A | H | $CH_3$ | $(CH_3)_2N$-sugar | $C_2H_5$ | $CH_3$ | $CH_3$ |
| A83543B | H | $CH_3$ | $(CH_3)NH$-sugar | $C_2H_5$ | $CH_3$ | $CH_3$ |
| A83543C | H | $CH_3$ | $H_2N$-sugar | $C_2H_5$ | $CH_3$ | $CH_3$ |
| A83543D | $CH_3$ | $CH_3$ | $(CH_3)_2N$-sugar | $C_2H_5$ | $CH_3$ | $CH_3$ |
| A83543E | H | $CH_3$ | $(CH_3)_2N$-sugar | $C_2H_5$ | $CH_3$ | $CH_3$ |
| A83543F | H | H | $(CH_3)_2N$-sugar | $C_2H_5$ | $CH_3$ | $CH_3$ |
| A83543G | H | $CH_3$ | $(CH_3)_2N$-sugar (3-O-CH_3) | $C_2H_5$ | $CH_3$ | $CH_3$ |
| A83543H | H | $CH_3$ | $(CH_3)_2N$-sugar | $C_2H_5$ | H | $CH_3$ |
| A83543J | H | $CH_3$ | $(CH_3)_2N$-sugar | $C_2H_5$ | $CH_3$ | H |

-continued

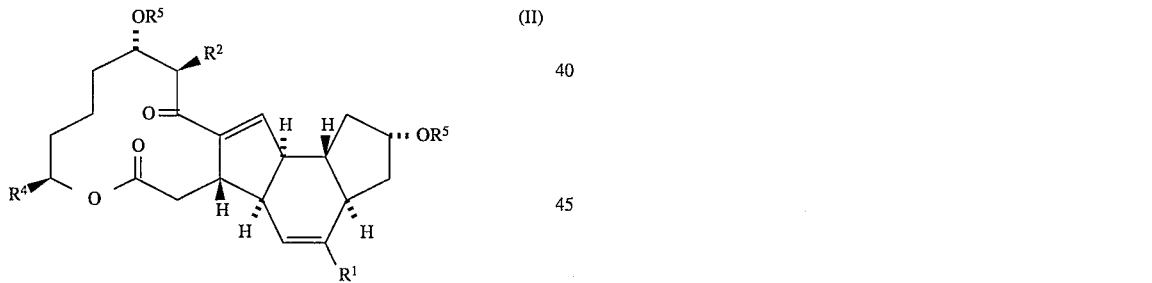

| Factor | $R^{1'}$ | $R^{2'}$ | $R^{3'}$ | $R^{4'}$ | $R^{5'}$ | $R^{6'}$ |
|---|---|---|---|---|---|---|
| A83543L | $CH_3$ | $CH_3$ | $(CH_3)_2N$—[sugar with $CH_3$, O] | $C_2H_5$ | $CH_3$ | H |
| A83543M | H | $CH_3$ | $(CH_3)NH$—[sugar with $CH_3$, O] | $C_2H_5$ | $CH_3$ | H |
| A83543N | $CH_3$ | $CH_3$ | $(CH_3)NH$—[sugar with $CH_3$, O] | $C_2H_5$ | $CH_3$ | H |
| A83543PsaA1 | H | $CH_3$ | H | $C_2H_5$ | $CH_3$ | $CH_3$ |
| A83543PsaD1 | $CH_3$ | $CH_3$ | H | $C_2H_5$ | $CH_3$ | $CH_3$ |
| A83543PsaE1 | H | $CH_3$ | H | $CH_3$ | $CH_3$ | $CH_3$ |
| A83543PsaF1 | H | H | H | $C_2H_5$ | $CH_3$ | $CH_3$ |
| A83543PsaH1 | H | $CH_3$ | H | $C_2H_5$ | H | $CH_3$ |
| A83543PsaJ1 | H | $CH_3$ | H | $C_2H_5$ | $CH_3$ | H |
| A83543PsaL1 | $CH_3$ | $CH_3$ | H | $C_2H_5$ | $CH_3$ | H |

SUMMARY OF THE INVENTION

This invention provides compounds of the formula (II)

wherein $R^1$, $R^2$, $R^3$, $R^4$, and $R^5$ are selected from the following combinations of values:

| Compound | $R^1$ | $R^2$ | $R^3$ | $R^4$ | $R^5$ |
|---|---|---|---|---|---|
| Compound 1 | H | $CH_3$ | $(CH_3)_2N$—[sugar with $CH_3$, O] | $C_2H_5$ | [sugar with $CH_3O$, $CH_3$, $OCH_3$, O] |
| Compound 2 | $CH_3$ | $CH_3$ | $(CH_3)_2N$—[sugar with $CH_3$, O] | $C_2H_5$ | [sugar with $CH_3O$, $CH_3$, $OCH_3$, O] |

-continued

| Compound | R¹ | R² | R³ | R⁴ | R⁵ |
|---|---|---|---|---|---|
| Compound 3 | H | CH₃ | (CH₃)NH— (sugar with CH₃, O) | C₂H₅ | (sugar with CH₃O, CH₃, OCH₃, O) |
| Compound 4 | CH₃ | CH₃ | (CH₃)NH— (sugar with CH₃, O) | C₂H₅ | (sugar with CH₃O, CH₃, OCH₃, O) |
| Compound 5 A83543PsaA2 | H | CH₃ | (CH₃)₂N— (sugar with CH₃, O) | C₂H₅ | H |
| Compound 6 A83543PsaD2 | CH₃ | CH₃ | (CH₃)₂N— (sugar with CH₃, O) | C₂H₅ | H |
| Compound 7 A83543PsaB2 | H | CH₃ | (CH₃)NH— (sugar with CH₃, O) | C₂H₅ | H |
| Compound 8 A83543PsaN2 | CH₃ | CH₃ | (CH₃)NH— (sugar with CH₃, O) | C₂H₅ | H |
| Compound 9 A83543AgA | H | CH₃ | H | C₂H₅ | H |
| Compound 10 A83543AgD | CH₃ | CH₃ | H | C₂H₅ | H |
| Compound 11 A83543AgE | H | CH₃ | H | CH₃ | H |
| Compound 12 A83543AgF | H | H | H | C₂H₅ | H |
| Compound 13 A83543PsaC2 | H | CH₃ | H₂N— (sugar with CH₃, O) | C₂H₅ | H |
| Compound 14 | CH₃ | CH₃ | H₂N— (sugar with CH₃, O) | C₂H₅ | H | or an acid addition salt thereof when R³ is other than hydrogen.

Aglycones of formula (II) wherein R¹ is H are prepared by acid hydrolysis of starting materials of formula (I) wherein R¹ is H, as illustrated in the following Scheme A.

Specific applications of this process are illustrated in Scheme B, and appropriate reaction conditions are illustrated in Example 1.

SCHEME A

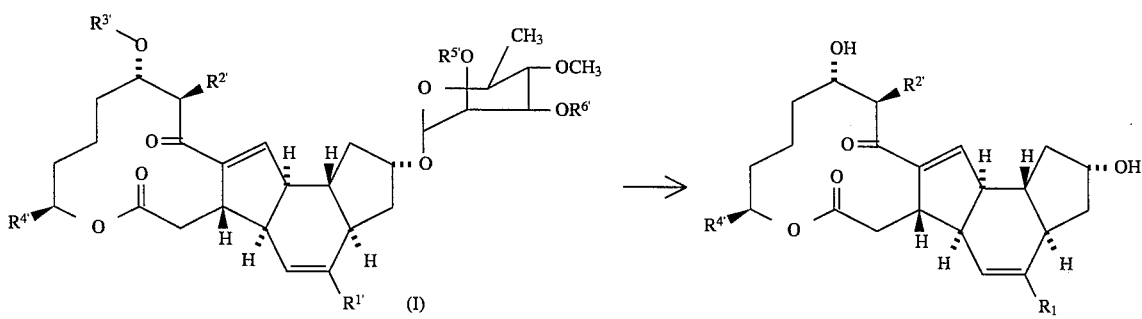

SCHEME B

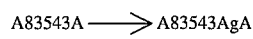
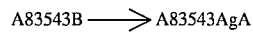
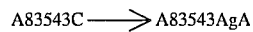
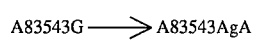
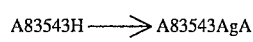
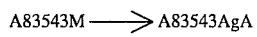
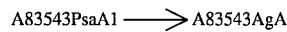
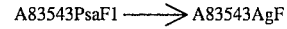

EXAMPLE 1

Preparation A83543AgA (Compound 9)

To a solution of A83543PsaA1 (6.03 g, 10.7 mmol) in methanol (267 mL), 7.2N $H_2SO_4$ (396 mL) was added, and the solution was heated to reflux for 3 hours. The mixture was then cooled in an ice bath. A large amount of $NaHCO_3$ (solid) and saturated aqueous $NaHCO_3$ were added cautiously; however, the pH was never brought above 1.0. The aqueous solution was mixed with ethyl ether and separated. The aqueous portion was then extracted with fresh ethyl ether. The ether extracts were combined, washed with brine, dried with $K_2CO_3$, and evaporated at reduced pressure. The resulting yellow semi-solid (4.89 g) was purified by normal phase chromatography with 100% dichloromethane and a gradient up to 7.5% methanol in dichloromethane, giving A83543AgA (2.83 g, 66% yield) as a colorless glass.

The procedure described in Schemes A and B and Example 1 is not suitable for preparation of A83543AgD, because starting materials of formula I wherein $R^1$ is methyl are prone to acid catalyzed skeletal rearrangement. Scheme C illustrates an alternative process that can be used to prepare A83543AgD and other compounds of the invention.

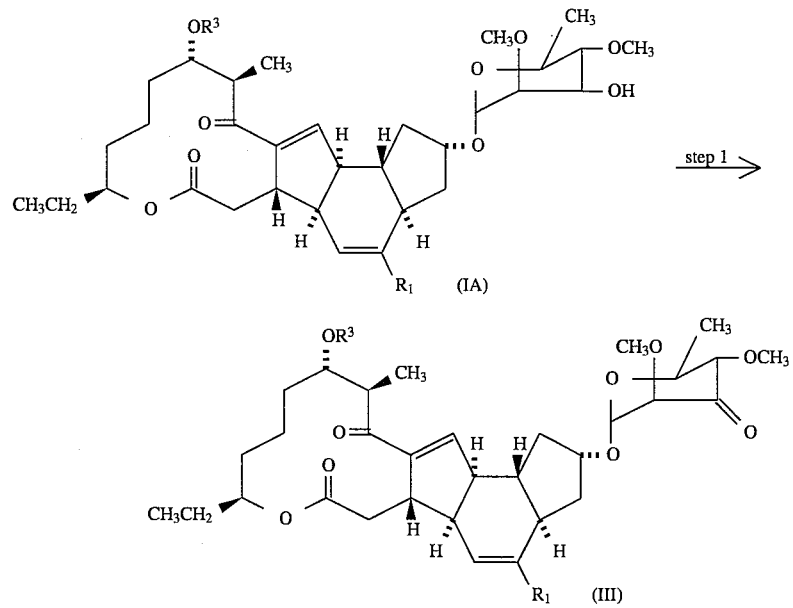

-continued
SCHEME C

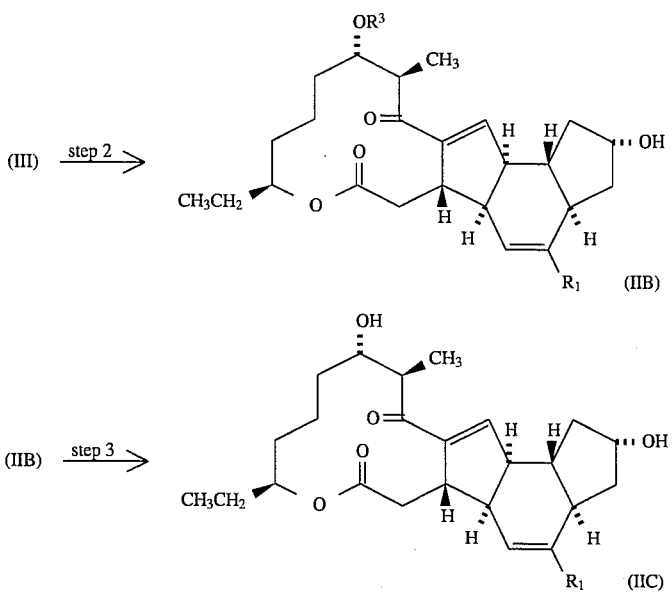

In step 1 of Scheme C, a compound selected from A83543J, A83543L, A83543M, and A83543N, represented by structure IA, is oxidized to deliver the corresponding intermediate of formula (III). An appropriate procedure for carrying out the oxidation is illustrated in the following Examples 2 and 3.

In step 2 of Scheme C, the intermediate of formula (III) is converted to the corresponding pseudoaglycone of formula (IIB). Appropriate reaction conditions for step 2 are illustrated in the following Examples 4 and 5.

In step 3 of Scheme C, a pseudoaglycone of formula (IIB) is hydrolyzed to provide the corresponding aglycone of formula (IIC). An appropriate procedure is illustrated in the following Example 6.

Specific applications of the procedure of Scheme C are illustrated in Scheme D.

SCHEME D

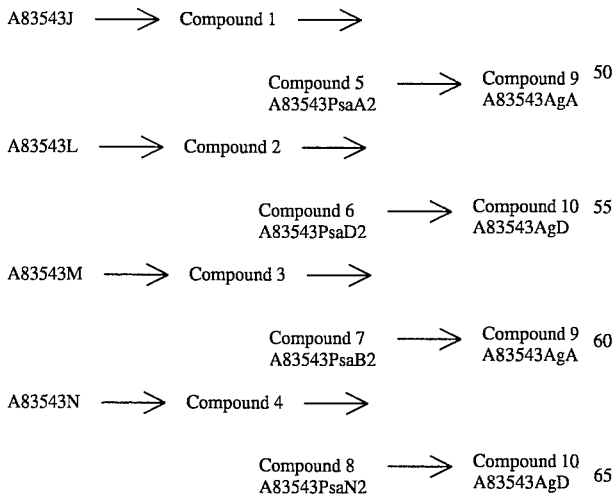

EXAMPLE 2

Preparation of Compound 1

A suspension of N-chlorosuccinimide (104.7 mg, 0.78 mmol) in dichloromethane (2.6 mL) was cooled to −78° C. under nitrogen. Diisopropyl sulfide (0.125 mL, 0.86 mmol) was added to this suspension, and the mixture was stirred at −78° C. for one half hour. A83543J (184.6 mg, 0.26 mmol) in dichloromethane (1 mL) was then added slowly. When the addition was completed, the solution was stirred at −78° C. for 6.25 hours. Triethylamine (0.109 mL, 0.78 mmol) was then added, and the solution was warmed to room temperature. The mixture was red. After warming, ethyl ether (6mL) was added and a precipitate formed. The precipitate was dissolved in dichloromethane, and this was combined with the ethyl ether solution. The resulting solution was washed with 0.1$\underline{N}$ HCl, then washed with brine, dried with $MgSO_4$, and evaporated at room temperature. The resulting colorless glass (215 mg) was semi-purified by flash chromatography with 5% methanol in dichloromethane, giving Compound 1 as a colorless semi-solid (151.2 mg). The weight recovery and NMR spectrum showed contamination of product with diisopropyl sulfide, but the product was used without further purification.

EXAMPLE 3

Preparation of Compound 2

The procedure used in Example 2 was repeated starting with A83543L (997.4 mg, 1.36 mmol), and gave Compound 2 as a colorless semi-solid (850 mg).

EXAMPLE 4

Preparation of A83543PsaA2 (Compound 5)

To a solution of Compound 1 (1.89 g, 2.64 mmol) in methanol (100 mL), $K_2CO_3$ (anhydrous; 1.82 g, 13.2 mmol) was added, and the mixture was stirred at room temperature for one hour. Ethyl ether (100 mL) was then added and the mixture was filtered. The filtrate was evaporated at room temperature, giving a yellow solid. The yellow solid was dissolved in dichloromethane, washed with water, then brine, and dried with $MgSO_4$. The dichloromethane was then evaporated at reduced pressure, giving a colorless semi-solid (1.53 g). This semi-solid was purified by flash chromatography with 5% methanol in dichloromethane to 10% methanol in dichloromethane in a one-step gradient, giving A83543PsaA2 (1.09 g, 76% yield) as an off white glass.

EXAMPLE 5

Preparation of A83543PsD2 (Compound 6)

The procedure described in Example 4 was repeated using as starting material the product of Example 2 (770 mg, 1.06 mmol) and producing A83543PsaD2 (246 mg, 42% yield) as a colorless glass.

EXAMPLE 6

Preparation of A83543AgD (Compound 10)

To a suspension of A83543PSaD2 (132 mg, 0.24 mmol) in water (5 mL), $1\underline{N}$ $H_2SO_4$ was added dropwise until the mixture had a pH of 1.7 and was homogeneous. This solution was heated to 80° C. for 3.75 hours, during which time an oil separated from the solution. The mixture was cooled to room temperature and dichloromethane was added to dissolve the oil. The aqueous layer was separated and extracted with fresh dichloromethane. The dichloromethane solutions were combined, washed quickly with $1\underline{N}$ $H_2SO_4$, dried with $K_2CO_3$, and evaporated at room tempeature giving a pale yellow glass (82.9 mg). The product was purified by flash chromatography with 5% methanol in dichloromethane, giving A83543AgD (63.6 mg, 63% yield) as a colorless glass.

Compounds 13 and 14 can be prepared by chemical demethylation of compounds 5 and 6, respectively, using sodium methoxide/iodine. The reaction is preferably carried out in a polar organic solvent, such as methanol. Further, the reaction is carried out at a temperature from about −10° C. to about 15° C., preferably between 0° C. and 5° C. The reaction times vary from about 4 hours to about 6 hours.

Accordingly, in another one of its aspects, the invention provides a process for producing A83543AgA, A873543AgD, A83543AgE, or A83543AgF, which comprises (a) hydrolyzing A83543A, A83543B, A83543C, A83543G, A83543H, A83543J, A83543PsaA1, A83543PsaA2, A83543PsaH1, A83543PsaJ1, A83543PsaB2, or A83543PsaC2 to produce A83543AgA; or (b) hydrolyzing A83543PsaD2 or A83543PsaN2 to produce A83543AgD; or (c) hydrolyzing A83543E or A83543PsaE1 to produce A83543AgE; or (d) hydrolyzing A83543F or A83543PsaF1 to produce A83543AgF.

The formula II compounds wherein $R^3$ is other than hydrogen can react to form acid addition salts, which are also a part of this invention. These salts are useful, for example, in separating and purifying the formula II compounds. These salts are prepared using standard procedures for salt preparation. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic, and like acids.

The compounds of this invention are useful as intermediates in the preparation of insecticides. For example, when appropriate microorganisms are cultured in the presence of the claimed compounds, the claimed compounds are bioconverted to insecticidally active A83543 factors, as illustrated by the following Example 7.

EXAMPLE 7

This example illustrates the preparation of A83543A by culturing NRRL 18538 in the presence of A83543AgA. The culture *Saccharopolyspora spinosa* NRRL 18538, either as a lyophilized pellet or as a suspension maintained in liquid nitrogen, was used to inoculate a vegetative medium having the following composition:

| Ingredient | Amount (g) |
| --- | --- |
| Enzyme-hydrolyzed casein | 30 |
| Yeast extract | 3 |
| $MgSO_4.7H_2O$ | 2 |
| Glucose | 10 |
| Deionized water | q.s. to 1 L |

The pH was ajusted to 6.5 with sodium hydroxide.

Slants or plates can be prepared by adding 2.5% agar to the vegetative medium. The inoculated slant is incubated at 30° C. for about 10 to 14 days. The mature slant culture is scraped with a sterile tool to loosen the spores and remove and macerate the mycelial mat. About one-fourth of the loosened spores and culture growth thus obtained is used to inoculate 50 mL of a first-stage vegetative medium. Alternatively, the first-stage medium may be inoculated from a liquid nitrogen ampoule.

When the culture is maintained in liquid nitrogen, ampoules are prepared using equal volumes of vegetative culture (48–72 hours incubation, 30° C.) and suspending medium. The suspending medium contains lactose (100g), glycerol (200 mL), and deionized water (q.s. to 1L).

A liquid nitrogen ampoule is used to inoculate 100 mL of vegetative medium in 500 mL erlenmeyer flasks (or 50 mL of medium in 250 mL flasks). The cultures are incubated at 30° C. for 48 hours on a shaker orbiting in a two inch (5.08 cm) circle at 250 rpm. The incubated culture (5% v/v inoculum) is used to inoculate 100 mL of a production medium having the following composition:

| Ingredient | Amount (g) |
| --- | --- |
| Glucose | 80 |
| Peptonized milk | 20 |
| Cottonseed flour | 30 |
| Corn steep liquor | 10 |
| $Ca_2CO_3$ | 5 |
| Methyl oleate | 30 |
| Tap water | q.s. to 1 L |

The pH was adjusted to 7.2 with sodium hydroxide.

Conversion of A83543AgA to A83543A was acomplished by addition of A83543AgA (4.88 mg, 0.195mg/mL) to a 65 hr culture of NRRL 18538 in the above mentioned production medium (25 mL in a 250 mL flask) and incubating the culture for an additional 31 hours. Acetonitrile (3.0 mL) was added to an aliquot (1.0 mL) of the culture. This sample was mixed and centrifuged and an aliquot was injected onto an analytical HPLC column designed to assay the various factors of the A83543 culture. Analysis of the fermentation broth showed the presence of 2.44 mg (0.098 mg/mL) of A83543A.

Using the same procedure, A83543AgD, A83543AgE, and A83543AgF can be bioconverted to A83543D, A83543E, and A83543F, respectively. Similarly, A83543PsaA2 can be bioconverted to known insecticide A83543A, A83543PsaD2 can be bioconverted to known insecticide A83543D, PsaB2 can be bioconverted to known insecticide A83543B, and PsaN2 can be biconverted to insecticide A83543N.

In another of its aspects the invention provides a method for converting A83543J and A83543L to A83543A and A83543D respectively, which comprises converting A83543J or A83543L to the corresponding aglycone, A83543AgA or A83543AgD, respectively, or to the corresponding pseudoaglycone, A83543A2 or A83543D2, respectively, and culturing NRRL 18538 in the presence of the aglycone or pseudoagylcone.

We claim:

1. A compound of the formula

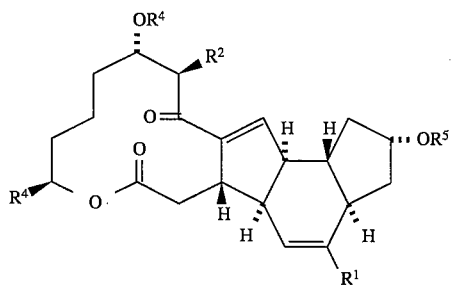

wherein $R^1$, $R^2$, $R^3$, $R^4$, and $R^5$ are selected from the following combinations of values:

| $R^1$ | $R^2$ | $R^3$ | $R^4$ | $R^5$ |
|---|---|---|---|---|
| H | $CH_3$ | $(CH_3)_2N$—[sugar]—O | $C_2H_5$ | H |
| $CH_3$ | $CH_3$ | $(CH_3)_2N$—[sugar]—O | $C_2H_5$ | H |
| H | $CH_3$ | $(CH_3)NH$—[sugar]—O | $C_2H_5$ | H |
| $CH_3$ | $CH_3$ | $(CH_3)NH$—[sugar]—O | $C_2H_5$ | H |
| H | $CH_3$ | H | $C_2H_5$ | H |
| $CH_3$ | $CH_3$ | H | $C_2H_5$ | H |
| H | $CH_3$ | H | $CH_3$ | H |
| H | H | H | $C_2H_5$ | H |
| H | $CH_3$ | $H_2N$—[sugar]—O | $C_2H_5$ | H |
| $CH_3$ | $CH_3$ | $H_2N$—[sugar]—O | $C_2H_5$ | H | or an acid addition salt thereof when $R^3$ is other than hydrogen.

2. The compound of claim 1 wherein $R^1$, $R^2$, $R^3$, $R^4$, and $R^5$ are H, $CH_3$, H, $C_2H_5$, and H, respectively, which is A83543AgA.

3. The compound of claim 1 wherein $R^1$, $R^2$, $R^3$, $R^4$, and $R^5$ are $CH_3$, $CH_3$, H, $C_2H_5$, and H, respectively, which is A83543AgD.

4. The compound of claim 1 wherein $R^1$, $R^2$, $R^3$, $R^4$, and $R^5$ are H, $CH_3$, H, $CH_3$, and H, respectively, which is A83543AgE.

5. The compound of claim 1 wherein $R^1$, $R^2$, $R^3$, $R^4$, and $R^5$ are H, H, H, $C_2H_5$, and H, respectively, which is A83543AgF.

6. The compound of claim 1 wherein $R^1$, $R^2$, $R^3$, $R^4$, and $R^5$ are H, $CH_3$,

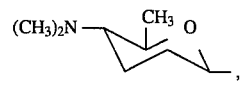

$C_2H_5$, and H, respectively, which is A83543PsA2.

7. The compound of claim 1 wherein $R^1$, $R^2$, $R^3$, $R^4$, and $R^5$ are $CH_3$, $CH_3$,

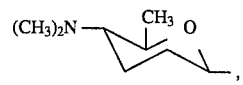

$C_2H_5$, and H, respectively, which is A83543PsD2.

8. The compound of claim 1, wherein $R^1$, $R^2$, $R^3$, $R^4$, and $R^5$ are selected from the following combinations of values:

| Compound | $R^1$ | $R^2$ | $R^3$ | $R^4$ | $R^5$ |
|---|---|---|---|---|---|
| Compound 5 (PsaA2) | H | Me | $(CH_3)_2N$—[sugar]—O | Et | H |
| Compound 6 (PsaD2) | Me | Me | $(CH_3)_2N$—[sugar]—O | Et | H |
| Compound 7 (PsaB2) | H | Me | $(CH_3)NH$—[sugar]—O | Et | H |
| Compound 8 (PsaN2) | Me | Me | $(CH_3)NH$—[sugar]—O | Et | H |
| Compound 10 (AgD) | Me | Me | H | Et | H |
| Compound 13 (PsaC2) | H | Me | $H_2N$—[sugar]—O | Et | H |
| Compound 14 | Me | Me | $H_2N$—[sugar]—O | Et | H | or an acid addition salt thereof when $R^3$ is other than hydrogen.

* * * * *

UNITED STATES PATENT AND TRADEMARK OFFICE
CERTIFICATE OF CORRECTION

PATENT NO. : 5,539,089

DATED : July 23, 1996

Page 1 of 2

INVENTOR(S) : Mary C. Broughton, Lawrence Creemer, Mary L. B. Huber, Herbert A. Kirst, Jan R. Turner It is certified that error appears in the above-indentified patent and that said Letters Patent is hereby corrected as shown below:

Cover page "[54] A83543 AGLYCONES AND PSEUDOGLYCONES" should read — [54] A83543 AGLYCONES AND PSEUDOAGLYCONES —.

Col. 1, line 1, "A83543 AGLYCONES AND PSEUDOGLYCONES" should read — A83543 AGLYCONES AND PSEUDOAGLYCONES —.

Col. 13, line 25, Claim 1, " 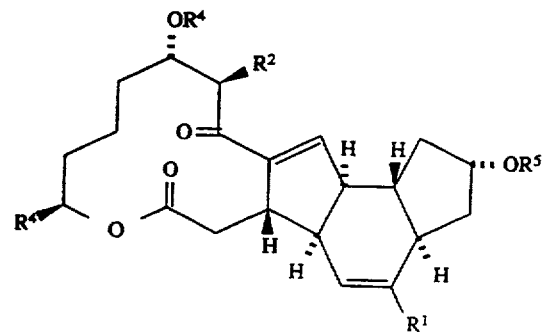 "

should read — 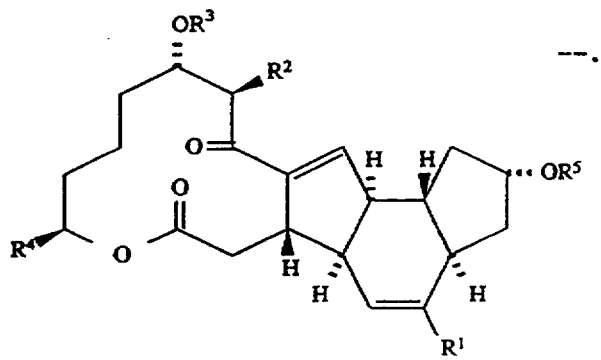 —.

UNITED STATES PATENT AND TRADEMARK OFFICE
CERTIFICATE OF CORRECTION

PATENT NO. : 5,539,089

DATED : July 23, 1996

INVENTOR(S) : Mary C. Broughton, Lawrence Creemer, Mary L. B. Huber, Herbert A. Kirst, Jan R. Turner It is certified that error appears in the above-identified patent and that said Letters Patent is hereby corrected as shown below:

should read —

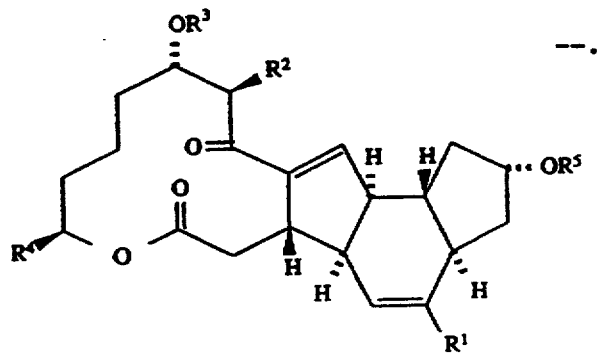

—.

Signed and Sealed this

Twenty-fifth Day of March, 1997

*Attest:*

BRUCE LEHMAN

*Attesting Officer*    Commissioner of Patents and Trademarks